United States Patent [19]

Hahn et al.

[11] Patent Number: 4,599,316

[45] Date of Patent: Jul. 8, 1986

[54] PHOTOMETRIC METHOD FOR THE DETERMINATION OF INORGANIC PHOSPHATE IN LIQUID SAMPLES

[75] Inventors: Benjamin A. Hahn, Yonkers, N.Y.; Richard A. Kaufman, Stanhope; Alexander F. Wesolowski, Florham Park, both of N.J.

[73] Assignee: Hoffmann-La Roche Inc., Nutley, N.J.

[21] Appl. No.: 557,710

[22] Filed: Dec. 2, 1983

[51] Int. Cl.$^4$ ............................................. G01N 21/78
[52] U.S. Cl. ................................... 436/105; 436/103; 436/164; 436/166
[58] Field of Search ................ 436/103, 105, 164, 166

[56] References Cited

U.S. PATENT DOCUMENTS

| | | | |
|---|---|---|---|
| 3,795,484 | 3/1974 | Daly et al. | 436/105 X |
| 3,796,543 | 3/1974 | Kamphake | 436/103 |
| 3,874,794 | 4/1975 | Schmitt et al. | 436/164 X |
| 3,874,853 | 4/1975 | Byrnes | 436/105 |
| 3,992,109 | 11/1976 | Bock | 436/164 X |
| 4,220,451 | 9/1980 | Stefanchik | 436/105 |
| 4,447,544 | 5/1984 | Neri et al. | 436/105 |
| 4,448,889 | 5/1984 | Neri et al. | 436/74 |
| 4,526,870 | 7/1985 | Muller | 436/164 X |

OTHER PUBLICATIONS

Lundgren, *Analytical Chemistry*, vol. 32, No. 7, pp. 824–828, Jun. 1960.
John A. Daly and Gerhard Ertingshausen, (1972), *Clinical Chemistry* vol. 18, No. 3, pp. 263–265.
Alex Wesolowski et al., *Clincal Chemistry* (1983), vol. 29, No. 6, Abstract No. 619.
Stanley M. Liffmann et al., *Clinical Chemistry* (1983), vol. 29, No. 6, Abstract No. 532.

*Primary Examiner*—Barry S. Richman
*Assistant Examiner*—Robert J. Hill, Jr.
*Attorney, Agent, or Firm*—Jon S. Saxe; George M. Gould; Norman C. Dulak

[57] ABSTRACT

An improved photometric method for the determination of inorganic phosphate in fluids is disclosed.

The method makes use of two reagents, an acid reagent and an ammonium molybdate reagent. Utilizing these reagents, the method comprises the following steps:

(a) forming a first mixture consisting of a sample fluid and acid reagent;
(b) measuring the light absorbance of said first mixture;
(c) forming a second mixture consisting of said first mixture and ammonium molybdate reagent;
(d) measuring the light absorbance of said second mixture;
(e) calculating the difference in light absorbance ($\Delta A$ sample) between the light absorbances measured for said first and second mixtures; and,
(f) determining the concentration of inorganic phosphate in said sample fluid by comparing the difference in light absorbance ($\Delta A$ sample) for said sample fluid to the difference in light absorbance ($\Delta A$ standard) for a standard fluid having a known concentration of inorganic phosphate, $\Delta A$ standard being determinable in a like manner to that set forth in steps (a)–(e).

4 Claims, No Drawings

PHOTOMETRIC METHOD FOR THE DETERMINATION OF INORGANIC PHOSPHATE IN LIQUID SAMPLES

FIELD OF THE INVENTION

This invention relates generally to a photometric method for the determination of inorganic phosphate in fluids, especially body fluids, as well as to reagents useful in the practice of this method. The method disclosed is particularly adapted for use with certain centrifugal photometric analyzers of known design.

BACKGROUND OF THE INVENTION

The majority of phosphorus (80–85%) present in the body is found in the bones as hydroxyapatite. The remainder is present as inorganic phosphate and phosphate esters. A determination of the concentration of inorganic phosphate in various body fluids can be highly useful in the diagnosis of various disease states. For example, increased serum phosphorus can be indicative of hypervitaminosis D. hypoparathyroidism, and renal failure. Similarly, reduced serum phosphorus levels are seen in rickets (Vitamin D deficiency), hyperparathyroidism, and Fancony's syndrome.

The inorganic phosphate content of body fluids has typically been determined using one of two known methods, or variations thereof. In the first method, that of Fiske and Subbarow [Biol. Chem. 66, 375 (1925)], a heteropoly compound formed between ammonium molybdate and inorganic phosphate is reduced under mild conditions to form the phosphomolybdenum complex, which is measured photometrically. In the second more widely used method, that of Daly and Ertingshausen [Clin. Chem. 18, 263 (1972)], inorganic phosphate is reacted with ammonium molybdate in sulfuric acid solution to form the unreduced phosphomolybdate complex, which is measured photometrically at about 340 nm.

Due to the immense volume of testing done by modern clinical laboratories, as well as the need for consistently accurate test results, inorganic phosphate determinations are typically performed using high speed, automatic instrumentation. In particular, the use of so-called centrifugal analyzers for the determination of inorganic phosphate has become widespread. An exemplary device of this type is described in U.S. Pat. No. 3,555,284.

Generally speaking, centrifugal photometric analyzers comprise an array of transparent reaction chambers or cuvettes arranged around the periphery of a centrifuge rotor. One or more solution receiving chambers are located radially inwardly from each cuvette and passageways are provided communicating between each cuvette and its associated solution receiving chambers. The solution receiving chambers are shaped to retain liquid when the rotor is at rest and to release liquids to the cuvettes when the rotor is spun. Thus, spinning of the rotor causes the transfer of sample, reagent or both to the cuvettes, where the samples and reagents react. As the rotor continues to spin, each cuvette passes, in turn, between a light source and a photodetector where the phototransmittance of the contents of each cuvette is read. These readings are then used to determine the concentration of a given species in each of the samples.

A typical prior art approach for the determination of inorganic phosphate utilizing a centrifugal analyzer is described in U.S. Pat. No. 3,795,484. In this method, which makes use of the unreduced phosphomolybdate complex chemistry described previously, samples under study are reacted in their respective cuvettes with a single reagent, which comprises ammonium molybdate, sulfuric acid and surfactant. Approximately two seconds after the rotor has begun to spin and, presumably, before the reaction has proceeded to a significant degree, a first or "blank" absorbance reading is taken for each cuvette. The purpose of this reading is to determine the inherent absorbance of the cuvette and unreacted sample and reagent. A second reading is taken after 10 minutes, the time required for the adequate reaction of sample and reagent. The change in absorbance between the first and second readings is compared to the change in absorbance obtained in a like manner for a standard having a known concentration of inorganic phosphate, in order to determine the phosphate content of each sample.

In an improvement of the above method, described in U.S. Pat. No. 4,220,451, a reduction of the time required for adequate reaction of sample and reagent—from 10 to about 2 to 4 minutes—is accomplished by optimizing the surfactant concentration of the reagent.

Although the above mentioned analytical methods certainly represent significant advances in the field of clinical chemistry, it will be appreciated that they nevertheless possess certain deficiencies. For example, in these prior methods the initial absorbance readings are not true blank readings, in that they are made after the reaction has already proceeded to an extent. Further, in view of the heavy workload of many clinical laboratories, the time required in these methods for reaction to proceed to an adequate extent and for a final reading to be taken, even at 2 to 4 minutes, is too long.

Accordingly, it is the object of this invention to provide an improved method for the determination of inorganic phosphate in fluids.

More particular objects are to provide an improved method for determining inorganic phosphate concentration which can be conveniently carried out using a centrifugal photometric analyzer, which allows for true sample blanking, and which is significantly more rapid than known methods.

SUMMARY OF THE INVENTION

The above and other objects are satisfied by the present invention which provides a method and reagents for the determination of inorganic phosphate utilizing a modification of the unreduced phosphomolybdate chemistry of Daly and Ertingshausen previously discussed. Although the method provided is particularly suitable for use with centrifugal analyzers, it should be recognized that it may also be practiced manually or adapted for use with other types of instrumentation.

In contrast to prior methods, the present method makes use of two reagents, an acid reagent and an ammonium molybdate reagent. Utilizing these reagents, the method comprises the following steps:

(a) forming a first mixture consisting of a sample fluid and acid reagent;

(b) measuring the light absorbance of said first mixture;

(c) forming a second mixture consisting of said first mixture and ammonium molybdate reagent;

(d) measuring the light absorbance of said second mixture;

(e) calculating the difference in light absorbance (Δ A sample) between the light absorbances measured for said first and second mixtures; and, (f) determining the concentration of inorganic phosphate in said sample fluid by comparing the difference in light absorbance (Δ A sample) for said sample fluid to the difference in light absorbance (Δ A standard) for a standard fluid having a known concentration of inorganic phosphate, Δ A standard being determinable in a like manner to that set forth in steps (a)–(e).

DETAILED DESCRIPTION OF THE INVENTION

As previously indicated, although the method provided by the invention can be carried out manually or using other instrumentation, it is intended primarily for use with centrifugal photometric analyzers of the type which are capable of adding at least two different reagents to a sample being tested. An exemplar of this type of machine is the COBAS BIO ® automated chemistry analyzer, manufactured by Hoffmann-La Roche Inc. Accordingly, the invention is described herein in terms of how it can be practiced in an exemplary fashion utilizing a centrifugal analyzer such as the COBAS BIO ®. Those skilled in the art will, of course, comprehend the manner in which the invention could be practiced manually or with other instrumentation.

As previously mentioned, two reagents are required for the practice of the invention, an acid reagent and an ammonium molybdate reagent.

While prior art techniques make use of a single reagent comprising ammonium molybdate, sulfuric acid and surfactant, it has been found that, in the practice of the present method, in order for a proper sample blank reading to be obtained, the pH during the sample blank reading should be about the same as that during the final transmittance reading. Accordingly, before taking the sample blank reading the sample is first diluted with the acidic reagent. Later, when molybdate reagent is added to this acid reagent/sample mixture, the acid takes part in the formation of the phospho-molybdate complex. It has been found possible to either place the full amount of acid required in the so-called acid reagent or to split the acid between both the acid and molybdate reagents.

In order to prevent precipitation where proteinaceous samples are used. The final mixture of both reagents and sample optimally contains a minor amount of a non-ionic surface-active agent such as Brij 35, Triton X-100, Triton 405, Tween 80 or Tween 20. This surfactant may be placed in either reagent or divided between the two.

An appropriate acid reagent would comprise an aqueous solution containing sulfuric acid, at a concentration ranging between about 0.05 and 0.34 moles per liter, and surfactant, at a concentration ranging between about 0 and 1.2 percent by volume.

An exemplary acid reagent contains about 0.255 moles per liter of sulfuric acid and about 0.8 percent by volume of Brij 35 surfactant.

An appropriate ammonium molybdate reagent would comprise an aqueous solution containing ammonium molybdate, at a concentration of about 0.0054 moles per liter, sulfuric acid, at a concentration ranging between about 0.93 and 0 moles per liter, and surfactant, at a concentration ranging between about 0 and 1.2 percent by volume.

An exemplary ammonium molybdate reagent contains about 0.0054 moles per liter of ammonium molybdate, and about 0.255 moles per liter of sulfuric acid.

In order to calculate the phosphate concentration of a sample, readings taken for the sample must be compared to those taken for one or more standards having known concentrations of phosphate. Readings taken for standards also serve as controls, verifying proper instrument operation. An advantageous aspect of the invention is that suitable inorganic phosphate standards can be either aqueous or protein based, regardless of whether the sample is aqueous or proteinaceous. It is preferred to utilize three separate standards. Suitable standards are available commercially or can be readily prepared by those skilled in the art using known per se techniques.

In the practice of the method provided by the invention, as it is performed using the COBAS BIO ® instrument, 5 μl aliquots of each of a number of sample fluids, as well as three standard phosphate solutions, are automatically drawn up, diluted with 50 μl portions of water, and pipetted into respective sample receiving chambers of a rotor. In order to provide a reagent blank reading, a 55 μl portion of water only is charged into one sample receiving chamber. Similarly, 150 μl portions of acid reagent are deposited in the reagent receiving chambers of the rotor. The rotor is then rapidly spun, centrifugally driving both the sample (or standard fluids) and the acid reagent into the peripherally diposed cuvettes, where the two combine to form a first mixture. In order to compensate for any endogenous sample interference, an initial absorbance reading, termed an "acid sample blank," is taken at this point as each cuvette passes through the machine's optical path. This reading can be taken in the range between about 320 and 380 nm., with 340 nm. being preferred. Rapid rotation of the rotor is then halted while the instrument automatically pipettes 50 μl portions of ammonium molybdate reagent, followed by 20 μl of water, into each sample receiving chamber of the rotor. Rapid rotation of rotor is again commenced, centrifugally driving the molybdate reagent into the cuvettes, where a second mixture consisting of sample or standard fluid and acid reagent (i.e. the previously formed first mixture) and molybdate reagent is formed. At this point, the following reaction takes place:

Inorganic phosphate + H₂SO₄ + Ammonium Molybdate ⟶

Unreduced phosphomolybdate complex

The reaction yielding the phosphomolybdate complex is conveniently carried at a temperature ranging between about 24° and 40° C., and preferrably is carried out at 37° C. The time required for the substantial completion of the reaction will, depending upon reaction temperature, range between about 10 and 50 seconds, with the time required at 37° C. being about 15 seconds.

At the completion of the complex forming reaction, a final absorption reading is taken for the second mixture in each cuvette.

Upon completion of the final absorption reading, the instrument calculates a factor using the following formula:

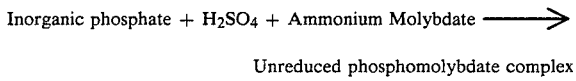

-continued $$\tfrac{1}{3}\left[\frac{conc(St_1)}{\Delta A(St_1) - \Delta A_{RB}} + \frac{conc(St_2)}{\Delta A(St_2) - \Delta A_{RB}} + \frac{conc(St_3)}{\Delta A(St_3) - \Delta A_{RB}}\right]$$

then:

Concentration of the sample (mg/dl)=($\Delta$A sample$-\Delta A_{RB}$)$\times$F where:

conc=Concentration in mg/dl
$St_1$=Standard One
$St_2$=Standard Two
$St_3$=Standard Three
$\Delta A$=Change in Absorbance
RB=Reagent Blank (Cuvette containing only 55 $\mu$l of water and reagent).

Note: $\Delta A_{RB}$ is normally a value close to zero.

It is to be understood that the foregoing description of the invention is by way of illustration and not of limitation and that persons of ordinary skill in the art may employ other embodiments without departing materially from the spirit or scope of the invention.

We claim:

1. A method for determining the concentration of inorganic phosphate in a sample fluid, said method comprising the steps of:
   (a) forming a first mixture comprising said sample fluid and an acid reagent and a surfactant;
   (b) measuring light absorbance of said first mixture;
   (c) forming a second mixture comprising said first mixture and ammonium molybdate reagent;
   (d) measuring light absorbance of said second mixture within about 10 to about 50 seconds after the formation thereof, wherein the temperature at which the second mixture is formed and concentrations of the acid and ammonium molybdate reagents are selected such that inorganic phosphate in the sample fluid substantially completely reacts with the ammonium molydbate reagent to form a phosphomolybdate complex prior to measuring light absorbance of said second mixture;
   (e) calculating a difference in light absorbance between the light absorbances measured in steps (b) and (d); and
   (f) determining the concentration of inorganic phosphate in said sample fluid by comparing the difference in light absorbance for said sample fluid to a difference in light absorbance for a standard fluid having a known concentration of inorganic phosphate, said difference in light absorbance for said standard being determinable in a manner as set forth in steps (a)–(e) but employing said standard instead of sample.

2. The method of claim 1 wherein said light absorbance measurements are made at about 340 nm.

3. A method as in claim 1 wherein the first mixture comprises an aqueous solution containing sulfuric acid as the acid reagent, at a concentration ranging between about 0.05 and 0.34 moles per liter, the surfactant being present at a concentration up to 1.2 percent by volume.

4. A method as in claim 3 wherein the ammonium molybdate reagent contains ammonium molybdate at a concentration of about 0.0054 moles per liter.

* * * * *